US009452429B2

(12) United States Patent
Ayliffe

(10) Patent No.: US 9,452,429 B2
(45) Date of Patent: Sep. 27, 2016

(54) METHOD FOR MUTIPLEXED MICROFLUIDIC BEAD-BASED IMMUNOASSAY

(71) Applicant: E. I. Spectra, LLC, Ketchum, ID (US)

(72) Inventor: Harold E. Ayliffe, Ketchum, ID (US)

(73) Assignee: E. I. SPECTRA, LLC, Ketchum, ID (US)

( * ) Notice: Subject to any disclaimer, the term of this patent is extended or adjusted under 35 U.S.C. 154(b) by 0 days.

(21) Appl. No.: 13/629,784

(22) Filed: Sep. 28, 2012

(65) Prior Publication Data

US 2014/0094377 A1   Apr. 3, 2014

Related U.S. Application Data

(63) Continuation-in-part of application No. PCT/US2012/000237, filed on May 7, 2012, and a continuation-in-part of application No. 12/985,536, filed on Jan. 6, 2011, now Pat. No. 8,616,048, which is a continuation-in-part of application No. 12/381,252, filed on Mar. 10, 2009, now Pat. No. 8,171,778, which is a continuation-in-part of application No. 11/800,167, filed on May 4, 2007, now Pat. No. 7,520,164, said application No. 12/985,536 is a continuation-in-part of application No. 12/378,757, filed on Feb. 19, 2009, now Pat. No. 8,072,603, which is a continuation-in-part of application No. 11/701,711, filed on Feb. 2, 2007, now Pat. No. 7,515,268, said application No. 12/985,536 is a continuation-in-part of application No. 12/936,243, filed on Oct. 4, 2010, now Pat. No. 8,182,635, application No. 13/629,784, which is a continuation-in-part of application No. 12/872,749, filed on Aug. 31, 2010, which is a continuation-in-part of application No. 12/699,745, filed on Feb. 3, 2010.

(60) Provisional application No. 60/798,155, filed on May 5, 2006, provisional application No. 60/764,697, filed on Feb. 2, 2006, provisional application No. 61/486,198, filed on May 13, 2011, provisional application No. 61/123,248, filed on Apr. 7, 2008, provisional application No. 61/124,121, filed on Apr. 14, 2008.

(51) Int. Cl.
| | | |
|---|---|---|
| C40B 30/04 | (2006.01) | |
| B01L 3/00 | (2006.01) | |
| G01N 15/12 | (2006.01) | |
| G01N 15/14 | (2006.01) | |
| G01N 15/10 | (2006.01) | |
| G01N 33/49 | (2006.01) | |

(52) U.S. Cl.
CPC .... *B01L 3/502715* (2013.01); *B01L 3/502761* (2013.01); *G01N 15/1056* (2013.01); *G01N 15/12* (2013.01); *G01N 15/1463* (2013.01); *B01L 2300/0645* (2013.01); *B01L 2300/0874* (2013.01); *B01L 2300/0887* (2013.01); *B01L 2400/0487* (2013.01); *G01N 33/49* (2013.01); *G01N 2015/1037* (2013.01); *G01N 2015/1062* (2013.01); *G01N 2015/1087* (2013.01)

(58) Field of Classification Search
CPC ...... G01N 27/26; G01N 15/16; G01N 27/00; G01N 33/68
USPC ........ 436/43; 422/417; 250/459.1; 73/61.71; 506/9
See application file for complete search history.

(56) References Cited

U.S. PATENT DOCUMENTS

| | | | |
|---|---|---|---|
| 2,656,508 | A | 10/1953 | Colter |
| 3,910,702 | A | 10/1975 | Corll |
| 4,130,754 | A | 12/1978 | Fosslien |
| 4,164,870 | A | 8/1979 | Scordato et al. |
| 4,352,558 | A | 10/1982 | Eisert |
| 4,488,814 | A | 12/1984 | Johnson |
| 4,873,875 | A | 10/1989 | Cork |
| 5,126,022 | A | 6/1992 | Soane et al. |
| 5,326,692 | A | 7/1994 | Brinkley et al. |
| 5,338,427 | A | 8/1994 | Shartle et al. |

(Continued)

FOREIGN PATENT DOCUMENTS

| | | |
|---|---|---|
| WO | WO 2005033283 A2 * | 4/2005 |
| WO | WO 2009126257 A1 * | 10/2009 |

OTHER PUBLICATIONS

Continuity Data Map, US Patent and Trademark Office, 2014, 1.*

(Continued)

*Primary Examiner* — Maria Leavitt
*Assistant Examiner* — Amy M Bunker
(74) *Attorney, Agent, or Firm* — Foster Pepper PLLC; P. G. Scott Born

(57) ABSTRACT

A method for performing multiplexed bead-based immunoassays using a microfluidic cassette capable of detecting a particle passing in substantially single file through an interrogation zone and generating a Coulter effect signal responsive to a characteristic of the particle. A fluid sample may be prepared by associating antibody-coated beads of different sizes to particles of interest. A first multiplexing option may be based on bead size, in which case the intensity of the Coulter signal is used to sort or characterize the particles. A second multiplexing option may be based on detection of Stokes' shift phenomena, or even simply emission intensity, in which case particles may be characterized responsive to intensity of the signal resulting from detection of radiation. The first and second multiplexing options may be employed together to populate an array of particle characteristics.

11 Claims, 14 Drawing Sheets

(56) References Cited

U.S. PATENT DOCUMENTS

| | | |
|---|---|---|
| 5,376,878 A | 12/1994 | Fisher |
| 5,459,406 A | 10/1995 | Louge |
| 5,516,564 A | 5/1996 | Root et al. |
| 5,691,157 A | 11/1997 | Gong et al. |
| 5,800,690 A | 9/1998 | Chow et al. |
| 5,933,707 A | 8/1999 | Ayliffe et al. |
| 6,045,676 A | 4/2000 | Mathies et al. |
| 6,091,975 A | 7/2000 | Daddona et al. |
| 6,159,748 A | 12/2000 | Hechinger |
| 6,169,394 B1 | 1/2001 | Frazier et al. |
| 6,285,807 B1 | 9/2001 | Walt et al. |
| 6,382,228 B1 | 5/2002 | Cabuz et al. |
| 6,396,584 B1 | 5/2002 | Taguchi et al. |
| 6,426,615 B1 | 7/2002 | Mehta |
| 6,437,551 B1 | 8/2002 | Krulevitch et al. |
| 6,440,725 B1 | 8/2002 | Pourahmadi et al. |
| 6,454,945 B1 | 9/2002 | Weigl et al. |
| 6,488,896 B2 | 12/2002 | Weigl et al. |
| 6,638,482 B1 | 10/2003 | Ackley et al. |
| 6,656,431 B2 | 12/2003 | Holl et al. |
| 6,663,353 B2 | 12/2003 | Lipscomb et al. |
| 6,674,525 B2 | 1/2004 | Bardell et al. |
| 6,703,819 B2 | 3/2004 | Gascoyne et al. |
| 6,794,877 B2 | 9/2004 | Blomberg et al. |
| 6,816,257 B2 | 11/2004 | Goix |
| 7,204,139 B2 | 4/2007 | Takayama |
| 7,223,363 B2 | 5/2007 | McNeely et al. |
| 7,223,371 B2 | 5/2007 | Hayenga et al. |
| 7,235,400 B2 | 6/2007 | Adey |
| 7,332,902 B1 | 2/2008 | Vermeire et al. |
| 7,392,908 B2 | 7/2008 | Frazier |
| 7,410,809 B2 | 8/2008 | Goix et al. |
| 7,417,418 B1 | 8/2008 | Ayliffe |
| 7,515,268 B1 | 4/2009 | Ayliffe et al. |
| 7,520,164 B1 | 4/2009 | Ayliffe |
| 7,579,823 B1 | 8/2009 | Ayliffe |
| 7,835,000 B2 | 11/2010 | Graves et al. |
| 8,072,603 B2 * | 12/2011 | Ayliffe et al. ............. 356/417 |
| 8,153,949 B2 | 4/2012 | Kiesel et al. |
| 8,188,438 B2 | 5/2012 | Li |
| 8,743,352 B2 | 6/2014 | Gong |
| 2002/0005354 A1 | 1/2002 | Spence et al. |
| 2002/0061260 A1 | 5/2002 | Husar |
| 2002/0117517 A1 | 8/2002 | Unger et al. |
| 2002/0149766 A1 | 10/2002 | Bardell et al. |
| 2003/0008410 A1 * | 1/2003 | Hechinger ............... 436/172 |
| 2003/0180965 A1 | 9/2003 | Yobas et al. |
| 2004/0037739 A1 | 2/2004 | McNeely et al. |
| 2004/0151629 A1 | 8/2004 | Pease et al. |
| 2005/0054078 A1 | 3/2005 | Miller et al. |
| 2005/0118705 A1 | 6/2005 | Rabbitt et al. |
| 2005/0255600 A1 | 11/2005 | Padmanabhan et al. |
| 2006/0073609 A1 | 4/2006 | Shimizu |
| 2007/0012784 A1 | 1/2007 | Mercolino |
| 2007/0183934 A1 * | 8/2007 | Diercks et al. ............ 422/100 |
| 2007/0238112 A1 * | 10/2007 | Sohn et al. ................. 435/6 |
| 2008/0202927 A1 * | 8/2008 | Kayyem et al. ...... 204/403.01 |
| 2009/0071225 A1 * | 3/2009 | Schilffarth ................ 73/1.02 |
| 2009/0189088 A1 | 7/2009 | Ayliffe et al. |
| 2009/0272179 A1 | 11/2009 | Ayliffe |
| 2009/0325217 A1 | 12/2009 | Luscher |
| 2010/0217172 A1 | 8/2010 | Hyde et al. |

OTHER PUBLICATIONS

Demeule et al., Characterization of Particles in Protein Solutions: Reaching the Limits of Current Technologies, The AAPS Journal, 2010, 12(4), 708-715.*

* cited by examiner

SECTION A-A

METHOD FOR MUTIPLEXED MICROFLUIDIC BEAD-BASED IMMUNOASSAY

PRIORITY CLAIM

This application is a continuation-in-part (CIP) of the International Patent Application (IPA) filed on May 7, 2012, under the Patent Cooperation Treaty (PCT), Serial No. PCT/US2012/000237, titled "METHOD FOR MULTIPLEXED MICROFLUIDIC BEAD-BASED IMMUNOASSAY", and claims the benefit of the filing date of United States (US) Provisional Patent Application (PPA) Ser. No. 61/486,198, filed May 13, 2011, titled "METHOD FOR MULTIPLEXED MICROFLUIDIC BEAD-BASED IMMUNOASSAY"; and is a CIP of U.S. utility application Ser. No. 12/985,536, filed Jan. 6, 2011, titled "REUSABLE THIN FILM PARTICLE SENSOR", now U.S. utility Pat. No. 8,616,048, which is a CIP of U.S. utility application Ser. No. 12/381,252, filed Mar. 10, 2009, titled "THIN FILM PARTICLE SENSOR", now U.S. utility Pat. No. 8,171,778, which is a CIP of U.S. utility application Ser. No. 11/800,167, filed May 4, 2007, titled "THIN FILM PARTICLE SENSOR", now U.S. utility Pat. No. 7,520,164, and claims the benefit under 35 U.S.C. 119(e) of the filing date of U.S. PPA Ser. No. 60/798,155, filed May 5, 2006, titled "THIN FILM PARTICLE SENSOR", and is a CIP of U.S. utility application Ser. No. 12/378,757, filed Feb. 19, 2009, titled "FLUORESCENCE-ACTIVATED CELL DETECTOR", now U.S. utility Pat. No. 8,072,603, which is a CIP of U.S. utility application Ser. No. 11/701,711, filed Feb. 2, 2007, titled "FLUORESCENCE-ACTIVATED CELL DETECTOR", now U.S. utility Pat. No. 7,515,268, and claims the benefit under 35 U.S.C. 119(e) of the filing date of US PPA Ser. No. 60/764,697, filed Feb. 2, 2006, titled "FLUORESCENCE-ACTIVATED CELL DETECTOR", and is a CIP of the U.S. utility application Ser. No. 12/936,243, now U.S. Pat. No. 8,182,635, which is a 35 USC 371 of the IPA filed on Apr. 7, 2009, under the PCT, Serial No. PCT/US2009/002172, titled "METHOD FOR MANUFACTURING A MICROFLUIDIC SENSOR", and claims the benefit under 35 U.S.C. 119(e) of the filing dates of U.S. PPA Ser. Nos. 61/123,248, filed Apr. 7, 2008 and 61/124,121, filed Apr. 14, 2008, both titled "METHOD FOR MANUFACTURING A MICROFLUIDIC SENSOR"; and is a CIP of U.S. utility application Ser. No. 12/872,749, filed Aug. 31, 2010, titled "MICROFLUIDIC CELL SORTER WITH ELECTROPORATION", which is a CIP of U.S. utility application Ser. No. 12/699,745, filed Feb. 3, 2010, titled "MICROFLUIDIC CELL SORTER AND METHOD", the entire disclosures of which are all hereby incorporated by this reference as though set forth in their entirety herein.

BACKGROUND

1. Field of the Invention

This invention relates generally to electrically-based, and/or optically based, sensors for use in detecting, quantifying, qualifying, or otherwise sensing, particles carried by a fluid. It is particularly directed to a method of use of a microfluidic sensor and interrogation structure for particle quantification and qualification.

2. State of the Art

Pioneering work in particle detection by measuring impedance deviation caused by particles flowing through a small aperture between two containers of electrically conductive fluid is disclosed in U.S. Pat. No. 2,656,508 to W. H, Coulter. Coulter's name is now associated with the principle of particles causing a change in electric impedance as they occlude a portion of the aperture. Since publication of his patent, considerable effort has been devoted to developing and refining sensing devices operating under the Coulter principle. Relevant US patents include U.S. Pat. No. 5,376,878 to Fisher, U.S. Pat. No. 6,703,819 to Gascoyne et al., U.S. Pat. No. 6,437,551 to Krulevitch et al., U.S. Pat. No. 6,426,615 to Mehta, U.S. Pat. No. 6,169,394 to Frazier et al., U.S. Pat. Nos. 6,454,945 and 6,488,896 to Weigl et al., U.S. Pat. No. 6,656,431 to Holl et al., and U.S. Pat. No. 6,794,877 to Blomberg et al. Patent application 2002/117,517 to Unger et al. is also relevant. Each above-referenced document is hereby incorporated by reference, as though set forth herein in their entireties, for their disclosures of relevant technology and structure employed in various sensor arrangements.

Flow cytometry is a well established technique that is used to determine certain physical and chemical properties of microscopic particles by sensing certain optical properties of the particles. Many books and articles are available detailing aspects of this useful investigational tool. For example, operational principles of, and procedures for use of, modern cytometers are set forth in "Practical Flow Cytometry" by Howard M. Shapiro, the contents of which are hereby incorporated by this reference. Flow cytometry is currently used in a wide variety of applications including hematology, immunology, genetics, food science, pharmacology, microbiology, parasitology and oncology.

In flow cytometry, microscopic particles entrained in a carrier fluid are typically arranged in single-file inside a core stream using hydrodynamic focusing. The particles are then individually interrogated by an optical detection system. The interrogation typically includes directing a light beam from a radiation source, such as a laser, transversely across the focused stream of single-file particles. The light beam is scattered by each particle to produce a scatter profile. The scatter profile may be analyzed by measuring the light intensity at both small and larger scatter angles. Certain physical and/or chemical properties of each particle can then be determined from the scatter profile.

It is also known to apply a biological label, such as one or more fluorescent tag, to selected particles of interest prior to processing such particles in a cytometer. For example, particles such as blood cells can be "tagged" with fluorescent molecules or small beads by using conjugated monoclonal antibodies. The wavelength of a radiation source (typically a laser), is matched to the excitation wavelength of the fluorescent tag. The tagged particles fluoresce in the cytometer, in accordance with a phenomena widely known as Stokes' shift, when excited by a laser beam. The fluorescence given off by the excited tag can be detected by an appropriately configured detector, which is conventionally mounted transverse to the path of the particles in the interrogation portion of the cytometer. Therefore, cells tagged with fluorescent markers can be easily detected for counting, or other data manipulation.

Unfortunately, flow cytometers are undesirably complex and expensive pieces of equipment. Care must be taken to ensure the machine is set up correctly, and properly calibrated. It would be an advance to provide a robust, inexpensive apparatus that can be used to promote single-file particle travel through an optically based interrogation zone to promote rapid processing of a plurality of different particle-bearing fluid samples.

While considerable progress has been made in sensor technology, a need remains for improved methods to interrogate particles. For example, it would be an improvement to provide methods for use of certain microfluidic structures to perform relatively simple, robust, and inexpensive multiplexed bead assays, including immunoassays.

BRIEF SUMMARY OF THE INVENTION

This invention provides methods for use of microfluidic sensors to perform multiplexed bead assays, non-exclusively including immunoassays. A preferred microfluidic sensor is structured to urge particles into substantially single-file travel through an interrogation zone. One preferred microfluidic sensor is embodied in a cassette, and includes a plurality of stacked thin film substantially planar layers providing structure defining a fluid path disposed inside the cassette. The fluid path provides an interrogation zone structured to urge particles traveling there-through into substantially single-file. Electrical structure included in the cassette permits interrogation of particles that travel through the interrogation zone in accordance with the Coulter principle. Optionally, the cassette may be adapted to permit simultaneous optical interrogation of such particles in the interrogation zone. Optical interrogation may include simply detecting a Stokes' shift emission, and/or measuring intensity of fluorescence. In some embodiments, a plurality of optical interrogations are performed simultaneously.

One method for interrogating particles entrained in a carrier fluid includes: providing a fluid sample containing particles that individually may carry one or more tag, label, or property indicative of one or more particle characteristic; providing a microfluidic test cassette; loading a first fluid sample into the cassette; installing the cassette in operable registration with an interrogation device; urging flow of the first fluid sample through the cassette while using the interrogation device to interrogate a portion of the first sample; and performing a multiplexed quantification of the particles in the interrogated portion.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

For convenience in this disclosure, the invention may sometimes be described with reference to particle detecting. Such description is not intended to limit the scope of the instant invention in any way. It is recognized that certain embodiments of the invention may detect passage of particles, e.g. for counting. Other embodiments may detect, determine, qualify, or quantify particle characteristics, such as size, or type, thereby permitting discrimination analyses. Furthermore, for convenience, the term "fluid" may be used herein to encompass a fluid mix including a fluid base formed by one or more diluents and particles of one or more types suspended or otherwise distributed in that fluid base. Particles are assumed to have a characteristic "size", which may sometimes be referred to as a diameter, for convenience. However, it should be recognized that an interrogated particle may be formed as a combination of constituent particles, including an analyte with one or more attached appropriately receptive bead. Currently preferred embodiments of the invention interrogate multi-sized populations of particles entrained in one or more fluid. Operable particles may include attached latex microspheres (beads), generally ranging in size from 0.5 µm to 35 µm in diameter, and this disclosure is structured accordingly. However, such is not intended to limit, in any way, the application of the invention to other fluids including fluids with particles having larger or smaller sizes.

In this disclosure, "single-file travel" is defined different than literally according to a dictionary definition. For purpose of this disclosure, substantially single-file travel may be defined as an arrangement of particles that are sufficiently spread apart and sequentially organized as to permit reasonably accurate detection of particles of interest. It is desirable to obtain true single particle detection at least about 80% of the time. When two particles are in the interrogation zone at the same, it is called coincidence, and there are ways to mathematically correct for it. Calibration may be performed using solutions having a known particle density (e.g. solutions of latex beads having a characteristic size similar to particle(s) of interest). Also, dilution of the particles in a fluid carrier may contribute to organizing particle travel. As a non-limiting example, it is currently preferred to use sensor devices structured to have sizes disclosed in this document for interrogation of fluid samples having a particle density of approximately between about $3 \times 10^3$ to about $2 \times 10^6$ cells/ml, where the particle size is on the order of the size of a red blood cell. The Coulter principle (and biology) require an electrically conductive fluid such as 0.9% saline. Solutions can be interrogated that have a particle density (particles/ml) between 1000/ml to 2,000,000/ml.

Figure 1A:
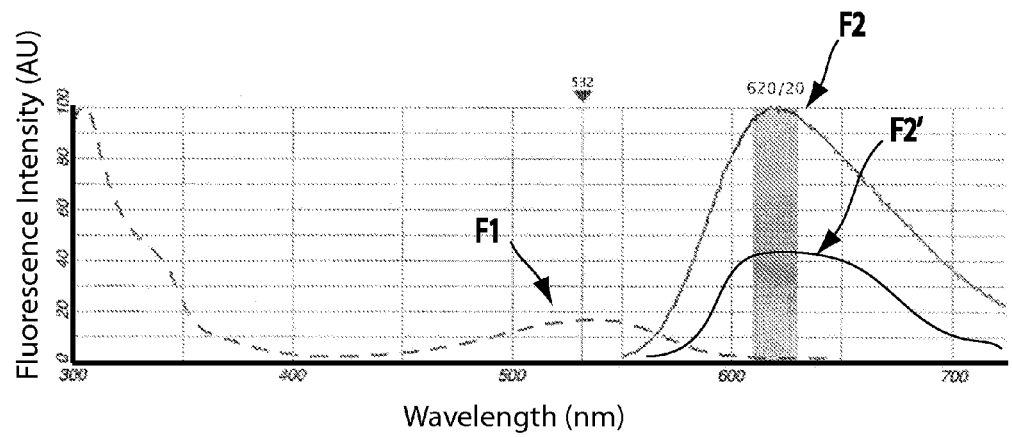
FIG. 1A is an X-Y plot of certain optical interrogation data obtainable using an embodiment of the invention.
Figure 1B:
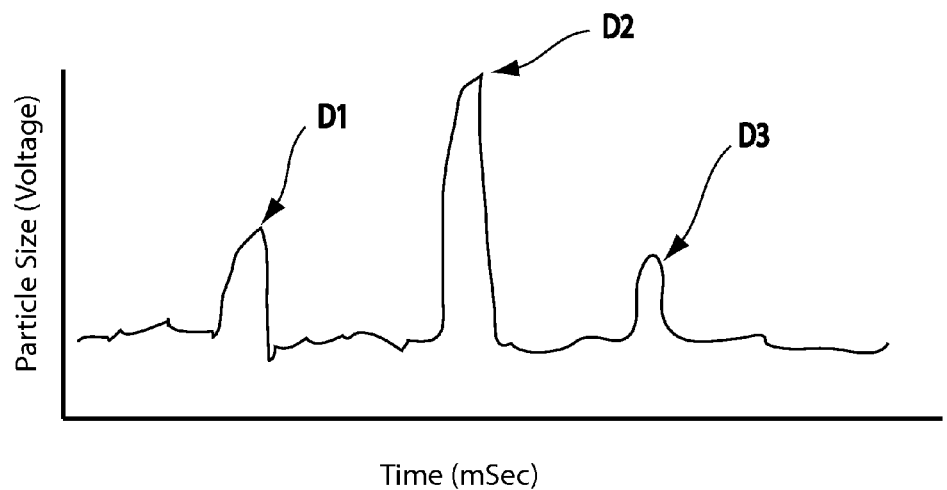
FIG. 1B is an X-Y plot of certain electrical interrogation data obtainable using an embodiment of the invention.
Figure 1C:
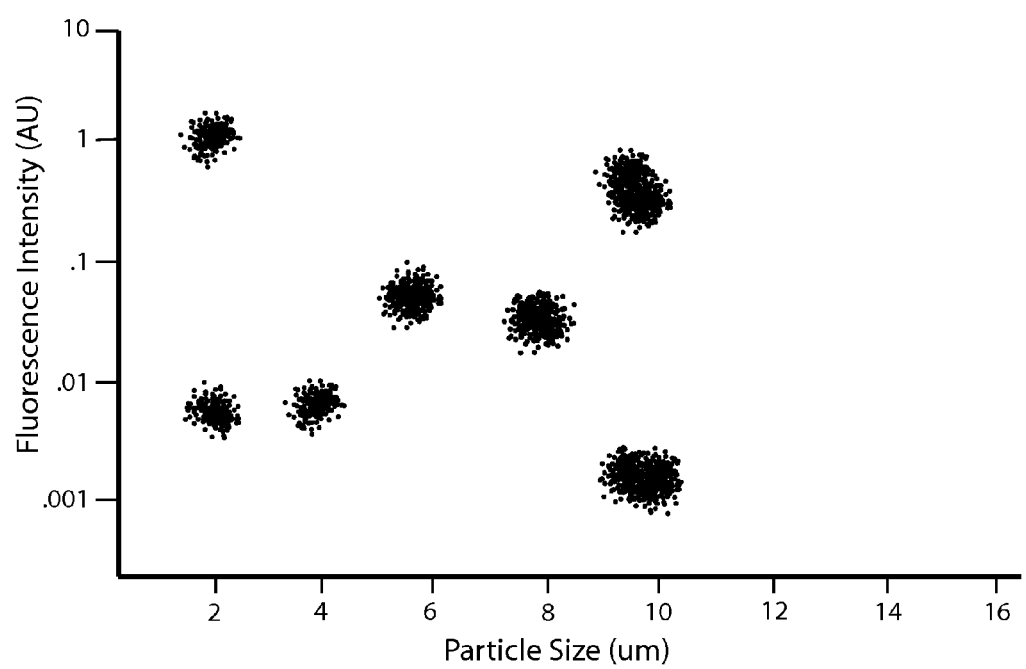
FIG. 1C is an X-Y scatter plot of certain qualification data obtainable using an embodiment of the invention.

FIGS. 1A through 1C illustrate exemplary data of the type that may be obtained using methods according to certain principles of the invention. It should be noted, for purpose of this disclosure, that the term "wavelength" is typically employed not necessarily with reference only to a single specific wavelength, but rather may encompass a spread of wavelengths grouped about a characteristic, or representative, wavelength. With reference to FIG. 1A, the characteristic wavelength F1 (e.g. excitation wavelength) of excitation radiation is sufficiently different from the characteristic wavelength F2 of the fluorescence (e.g. emission wavelength) to enable differentiation between the two. Furthermore, the difference between such characteristic wavelengths, or Stokes-shift differential, is desirably sufficiently different to enable, in certain embodiments, including a selective-pass filter element between a radiation source and detector effective to block transmission of excitation radiation toward a detector, while permitting transmission of the fluorescence "wavelength" through a selective-pass filter and to the detector. The magnitude of measured intensity may be used as one characteristic effective to distinguish between different markers, or tag elements, as exemplified by F2 and F2'.

With reference to FIG. 1B, the amplitude of measured impedance may be used to distinguish between particles having different sizes. A certain amount of noise is typically present in the raw signal, although various filter arrangements may reduce or eliminate the noise. The X-Y plot in FIG. 1B indicates first, second, and third particle sizes D1, D2, and D3, respectively. FIG. 1C illustrates one data characterization plot, wherein particle size and measured intensity indicate one or more characteristic of the interrogated sample.

Tiny beads, called microspheres, may be color-coded to form an interrogation set. A color may be assigned to a bead set by filling or coating the beads in that set with a dye combination that produces a distinct color or spectral emission when excited by a radiation source. An appropriately-receptive bead will bind to desired particulate matter of interest. Each bead set can be surface treated, or coated, with a reagent specific to a particular bioassay, allowing the capture and detection of specific analytes from a sample. Workable capture reagents include one or more of: antibodies, aptimers, proteins, oligonucleotides, peptides, and receptors. Particles such as blood cells can be "tagged" with fluorescent molecules or small beads by using conjugated monoclonal antibodies or polyclonal antibodies and potentially aptamers. Once the capture reagents are bound to the beads, a fluorescence reporter is added and binds specifically to the analyte of interest, or some directly related components thereof. Inside an interrogation platform, a light source excites the internal dyes that identify each microsphere-bound particle, and also any reporter dye captured during the assay. Classification and reporter readings may be made on each particle moving in single-file through an interrogation zone to determine multiplexed assay results.

Bead sizes can range from perhaps 0.5 µm to 35 µm in diameter, or so. Typical beads sizes used simultaneously (i.e., multiplexed) may be selected to include, for example, beads having 4, 6, 8, 10, 12, and 15 µm sizes. The difference between the listed sizes provides 6 groups of beads that are distinguishable from each other. Each size is typically individually prepared with different chemistries (i.e., characteristic emission, antigen coating, etc.) to form one or more sub-population of beads. A sub-population may be bead size-specific, and/or coating-specific. A plurality of sub-populations may then be mixed together and added to a slurry of cells (often lysed cells), to permit binding one or more microsphere to an analyte particle. The resulting mixture of bound particles may then be interrogated in a cassette and interrogation platform in accordance with certain principles of the instant invention. Most users purchase prepared cocktails of beads for specific investigations/analyses. However, some researchers prepare their own multiplexed bead mixtures.

In general, the instant invention applies to: Kinase sensitivity; autoimmune; hormones; cytokines/chemokines; allergen screening; and pharmacogenomics. The invention may be specifically applied to: DNA assays; Immunoassays; Receptor-ligand assays; and Enzyme assays, among other applications. Advantages of bead-based assays according to certain principles of the instant invention over conventional (2D) assays such as ELISA include: solution phase (3D) vs. solid phase (2D); reaction speed is much faster; smaller sample volumes; and high throughput/high content.

As one non-limiting example, groups of latex beads can be "tagged" with one dye color (e.g. wavelength) that is impregnated into each individual bead of the group. This first color is used to identify the bead group to which it belongs. The concentration of the impregnated dye can be altered to create different sub-groups of beads having specific concentrations of this first dye. This creates, for example, 5 sub-groups of beads (all with the same diameter and emission color, but different color intensity). Each of these five sub-groups has a slightly different dye concentration, producing different emission intensities that can be measured by a radiation detector to identify to which sub-group any particular bead belongs. It is within contemplation also to create different groups of beads based on size. Assume, for this example, that 5 different groups are created based upon bead size. Now, each of these "groups" of treated beads (5 sized-based and 5 fluorescence intensity-based; 5×5=25) can be prepared with a different surface chemistry (i.e., coated with antigens, proteins, etc.). This is the basis for "multiplexing". Each bead has a maximum number of receptors on its surface that attempt to bind to the analyte of interest in the sample being tested. The groups of treated beads are mixed into the sample being tested. Depending on the concentration of the analyte of interest, X number (of the analyte molecules) will bind to each bead. A fluorescent molecule (of a color that is distinguishable from the group-defining color) is attached to each of the bound analyte molecules (to light them up when stimulation radiation is applied). So, each individual bead can indicate the concentration of the analyte of interest in the sample. Further, each sub-group of beads can be used to measure something different in the sample (i.e., some other analyte).

Figure 2:
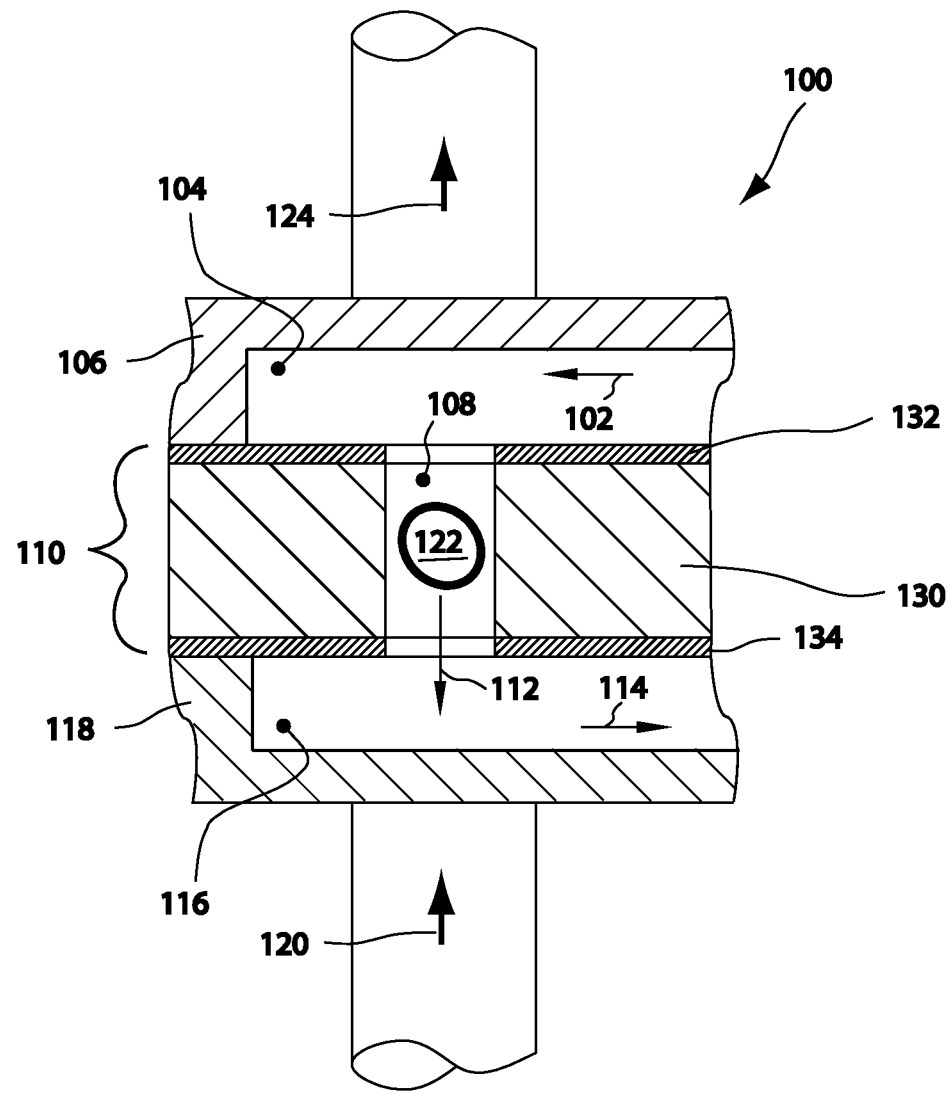
FIG. 2 is a cross-section view in elevation of a workable cassette for use with certain embodiments of the invention.

FIG. 2 illustrates portions of a device, generally indicated at 100, operable to optically interrogate one or more particle of interest as that particle travels through an interrogation zone in accordance with certain principles of the invention. Device 100 is illustrative of a microfluidic arrangement effective to urge particles of interest into substantially single-file travel through the interrogation zone. Fluid flows, as indicated by arrow 102, along a channel 104 carried in top layer 106. A tunnel 108 is structured to urge particles into substantially single-file travel through the interrogation layer 110. A tunnel 108 acts as an orifice operable to regulate fluid flow, among other effects. Fluid flow, indicated by arrow 112, through the tunnel 108 is approximately orthogonal to fluid flow 102 in channel 104. Fluid flow continues, as indicated by arrow 114, along channel 116 formed in bottom layer 118. It should be noted that channels may be formed in a layer, e.g. by machining or etching, or may be formed in separate stacked and bonded layers.

In the transverse optical interrogation arrangement illustrated in FIG. 2, the interrogation zone encompasses an area in channel 104 disposed at the entrance to tunnel 108. Similarly, the optical interrogation zone also encompasses an area in channel 116 at the exit of tunnel 108. Therefore, the height of the channels 104, 116, and characteristic size of the tunnel 108 desirably cooperate to resist clumping of particles in the interrogation zone, or to otherwise block transmission of either excitation radiation toward the particles of interest, or stimulated radiation toward a detector device. Excitation radiation, indicated by arrow 120, is directed to impinge on the interrogation zone. A particle of interest 122, which undergoes a Stokes' shift, emits stimulated radiation indicated by arrow 124. The stimulated radiation 124 can then be detected by an appropriate instrument, such as a photomultiplier tube (PMT).

It is currently preferred for the top layer 106 and the bottom layer 118 to be substantially transparent to optical radiation in a transverse through-the-thickness arrangement such as illustrated in FIG. 2. The uninterrupted portion of the interrogation layer 110 is preferably substantially opaque to all optical radiation. As illustrated, a workable interrogation layer 110 may be formed as a composite of two or more layers effective to at least substantially resist transmission of stimulation radiation there-through. An interrogation layer 110 may include a transparent substrate layer 130 carrying one or more opaque coating, such as metallized top coating 132 and metallized bottom coating 134. However, an interrogation layer may also constitute a single layer that inherently resists transmission therethrough of optical radiation. In certain cases, top layer 132 and/or bottom layer 134 may also function as an electrode in an arrangement effective to detect the Coulter effect. Furthermore, excitation radiation may sometimes be directed for transmission into the interrogation zone in the plane of, and through, the substrate layer 130.

Figure 3:
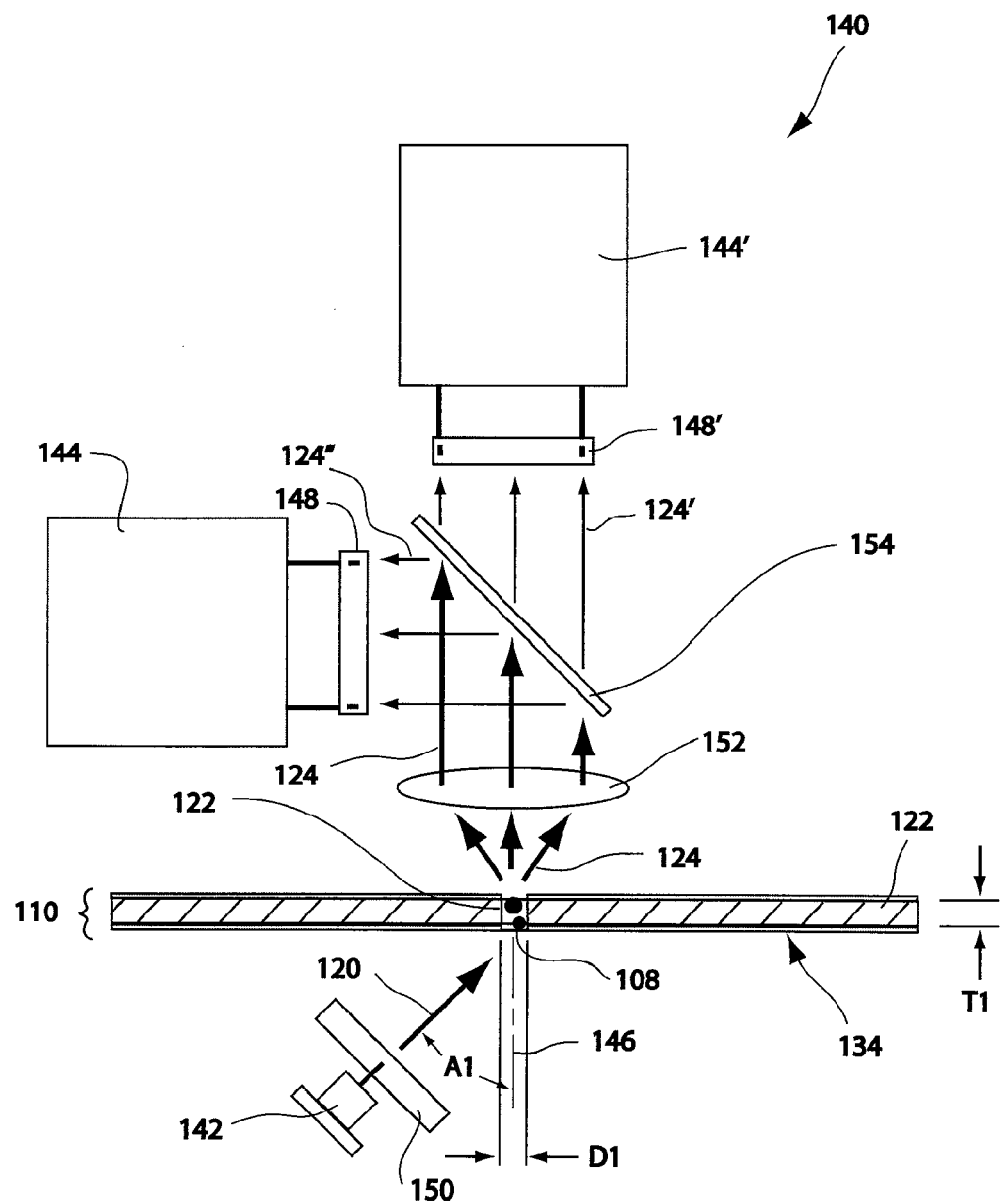
FIG. 3 is a cross-section view in elevation illustrating an arrangement effective to simultaneous quantify tag intensity and characterize analyte in an interrogation zone.

With reference now to FIG. 3, an arrangement of structures illustrating certain principles of operation of the invention is indicated generally at 140. As illustrated, embodiment 140 includes an opaque member 110 disposed between a radiation source 142 and at least one radiation detector 144. Opaque member 110 is provided as a portion of structure arranged to cause a desired fluid flow of a fluid sample including biological particles of interest. Sometimes, opaque member 110 may be made reference to as an interrogation layer, because layer 110 is associated with an interrogation zone associated with orifice 108. Orifice 108 may be characterized as having a through-axis 146 along which fluid may flow between the first and second sides of opaque member 110, respectively.

The thickness, T1, of an opaque member and characteristic size, D1, of an orifice 108 are typically sized in agreement with a size of a particle of interest to promote single-file travel of the particle through the opaque member, and to have substantially only one particle inside the orifice 108 (or in the interrogation zone) at the same time. In the case where the apparatus is used to interrogate multi-sized population of latex beads, the thickness of the opaque member may typically range between about 10 microns and about 300 microns, with a thickness of about 76 microns being currently preferred. The diameter, or other characteristic size of the orifice 108, may range between about 2 and 200 microns, with a diameter of about 44 microns being currently preferred for analysis and/or manipulation of multi-sized population of latex beads.

An operable opaque member 110 may function, in part, to reduce the quantity of excitation radiation 120 that is emitted by source 142, which is received and detected by a radiation detector 144. Excitation radiation 120 is illustrated as a vector having a direction. Desirably, substantially all of the excitation radiation 120 is prevented from being detected by the radiation detector 144. In any case, operable embodiments are structured to resist saturation of a detector 144 by excitation radiation 120. In certain embodiments, excitation radiation 120 may simply pass through orifice 108 for reception by the radiation detector 142. Therefore, certain embodiments may employ one or more selective radiation filter 148 as a measure to control radiation received by detector 106. Alternatively, certain embodiments may be structured to direct excitation radiation 120 at an angle (e.g. A1) with respect to the axis 146.

The opaque member 110 illustrated in FIG. 3 includes a core element carrying a first coating disposed on first side, and a second coating disposed on second side. An alternative core element may be formed from a core element having a coating on a single side. The illustrated coatings cooperatively form a barrier to transmission of excitation radiation through the core element. Of course, it is also within contemplation to alternatively use a bare core element that is, itself, inherently resistant to transmission of radiation. One currently preferred core includes opaque polyamide film that transmits very little light through the film, so no metallizing, or other barrier element, is required. However, certain embodiments may even have an interrogation layer 110 that is substantially transparent to excitation radiation 120, and can be employed as a conductor to introduce excitation radiation into an interrogation zone in a direction transverse to axis 146.

A workable core for use in detecting small sized particles can be formed from a thin polymer film, such as PET having a thickness of about 0.005 inches. Such polymer material is substantially permeable to radiation, so one or more coatings can be applied to such core material, if desired. A workable coating includes a metal or alloy of metals that can be applied as a thin layer, such as by sputtering, vapor deposition, or other well-known technique. Ideally, such a layer should be at least about 2-times as thick as the wavelength of the excitation radiation, e.g. about 1 μm in one operable embodiment. The resulting metallized film may be essentially impervious to transmission of radiation, except where interrupted by one or more orifice 108. Aluminum is one metal suitable for application onto a core substrate as a coating to resist transmission of radiation. Certain coatings may also be patterned and arranged to function as electrodes, conductive traces, and surface contact electrical pads.

The apparatus 140 illustrated in FIG. 3 is configured to urge a plurality of particles 122 in substantially single-file through orifice 108. A particle 122 typically passes through an excitation zone as the particle closely approaches, passes through, and recently departs from the orifice 108. Of note, the direction of particle-bearing fluid flow in FIG. 3 may be in either direction through orifice 108.

With reference still to FIG. 3, the opaque member 110 in embodiment 140 may essentially be disposed in a suitably sized container that is divided into two portions by the opaque member. Flow of fluid (and particles entrained in that fluid) through the orifice 108 could be controlled by a difference in pressure between the two divided portions. However, it is typically desired to provide more control over the flow path of particles in the vicinity of the orifice 108 than such an embodiment would permit. For example, a clump of particles disposed near an entrance or exit of the orifice 108 could shield a particle of interest from the excitation radiation 120 to the extent that fluorescence does not occur, thereby causing a miscount, or preventing detection of such a shielded particle of interest. Therefore, it is preferred to provide a channel system to control flow of fluid in the vicinity of the orifice 108 and form a robust interrogation zone.

Sometimes, and as illustrated in FIG. 3, it is preferred to apply excitation radiation 120 at an acute angle A1 to axis 146 of orifice 108. In such case, the opaque member 110 may even function substantially as an operable filter to resist direct transmission of excitation radiation 120 to a radiation detector. As illustrated, radiation vector 120 can be oriented to pass through, or partially into, orifice 108 without being detected by a radiation detector 144. However, when a stimulated particle 122 is present in an excitation zone (such as illustrated orifice 108), any resulting fluorescence 124 may still be detected by a radiation detector 144. While a workable angle A1 may be between 0 and 90 degrees, it is currently preferred for angle A1 to be between about 15 and about 75 degrees.

A radiation source 142 may be formed from a broad spectrum radiation emitter, such as a white light source. In such case, it is typically preferred to include a pre-filter 150 adapted to pass, or transmit, radiation only in a relatively narrow band encompassing the characteristic value required to excite a particular fluorescing agent associated with a particle of interest. It is generally a good idea to limit the quantity of applied radiation 120 that is outside the excitation wavelength to reduce likelihood of undesired saturation of the radiation detector 144, and consequent inability to detect particles of interest.

In one embodiment adapted to interrogate multi-sized population of latex beads, it is workable to use a red diode laser, and to include a short pass filter (after the diode laser), or excitation filter, that passes excitation light radiation with wavelengths shorter than about 642 nm. Another workable embodiment uses a green diode laser, and includes a short pass filter, or excitation filter, that passes excitation light radiation with wavelengths shorter than about 540 nm. The preferred embodiment includes a 488 nm blue laser. Laser line filters, sometimes termed laser clean-up filters, can also be used with the blue 488 nm diode lasers. It is currently preferred to include a band pass filter (e.g. just prior to a photodetector) with a peak that matches a particular selected fluorescence peak. Commercially available dyes may be obtained having characteristic fluorescent peaks at 600, 626, 660, 694, 725, and 775 nanometers. Long pass filters may be used in place of band-pass filters prior to the photodetector to resist transmission of excitation radiation, but pass emission radiation.

With continued reference to FIG. 3, sometimes it is preferred to include some sort of emission filter 148 that resists transmission of radiation outside the characteristic wavelength of the fluorescence 124. Such an arrangement reduces background noise and helps to avoid false readings indicative of presence of a particle of interest in an excitation zone. Also, to assist in obtaining a strong signal, an optical enhancement, such as a lens 152, can be included to gather and collate fluorescence 124 and direct such radiation toward a radiation detector 144. Illustrated lens 152 may be characterized as an aspheric collecting lens (or doublet), and typically is disposed to focus on a point located inside the orifice 108.

Sometimes, and as illustrated in FIG. 3, a plurality of radiation detectors 144, 144' are employed simultaneously to interrogate the same particle in the same interrogation zone. In such case, emission radiation 124 may be divided 124', 124" between the individual radiation detectors 144, 144' by a splitter, such as illustrated dichroic mirror 154. The arrangement illustrated in FIG. 3 permits detection, quantification, and/or qualification of different spectra (e.g. corresponding to fluorophore type and intensity), by selectively splitting the emitted light 124 in two directions based on a selected cut-off wavelength.

The dichroic mirror 154 works to reflect light with wavelengths shorter than a desired cutoff and allow longer wavelength light to pass right through. Such a mirror is a convenient way to split the light signal preferentially between two photo detectors. In this way, the same latex particle may be labeled, or impregnated, with two or more different fluorophores. The signal intensity from one of the colors (one of the fluorophores) can be used to determine which sub-population the bead belongs to (i.e., what the biological label of interest is) and the intensity of the second or other color (another fluorophore) can be used to determine the quantity of (for example) one or more analyte of interest that bound to the latex particle.

When variation in the bead size is added as a further variable, it is possible to multiplex a very large number of sub-populations of beads. Consequently, multiple populations of beads (each group having a unique size) can be prepared with one or more specific antigens on their surface. Each different sized bead population is prepared separately with a desired coupling reagent specific to the biological reaction of interest (i.e., antibodies, oligonucleotides, peptides, receptor). The biological samples are typically blood, suspensions of cells, or cocktails containing lysed cells. By preparing different sized beads with different surface reaction chemistries, it is possible to combine the multi-sized beads into a single cocktail and mix this cocktail with the biological sample being tested to run a parallel (or multiplexed) immunoassay. The biological sample being tested is prepared with the multisized bead cocktail and the fluorescent markers necessary to quantify the protein levels that bind to the modified latex beads. When the complete sample is run through the interrogation system, bead size is used to differentiate which chemistry (or coupling reagent) is being tested and the corresponding fluorescence intensity is used to quantify the reaction being tested. The addition of a second fluorophore at varying intensities (typically impregnated into the latex bead) can be used to create additional populations of beads with unique surface preparations.

Figure 4:
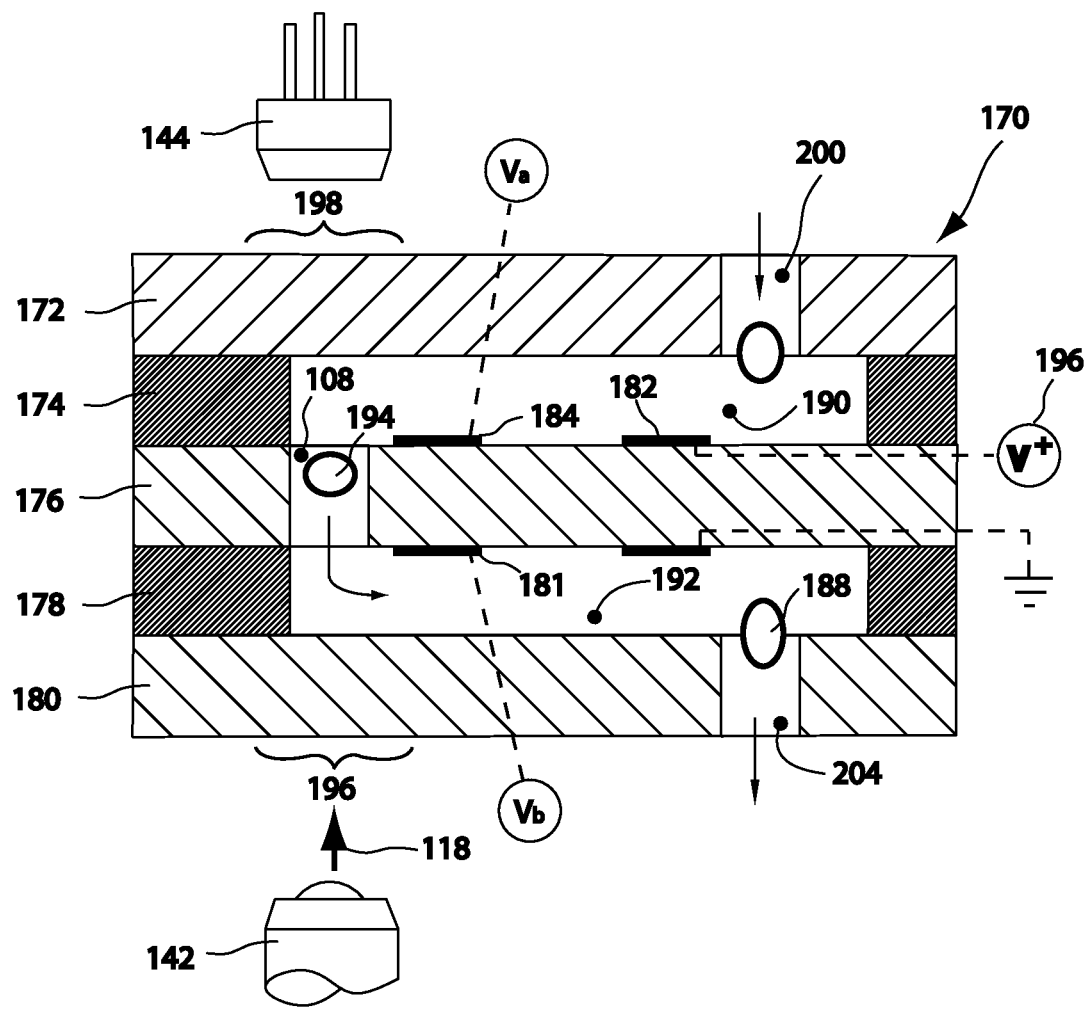
FIG. 4 is a cross-section view in elevation of an alternatively structured workable cassette for use with certain embodiments of the invention.
Figure 5:
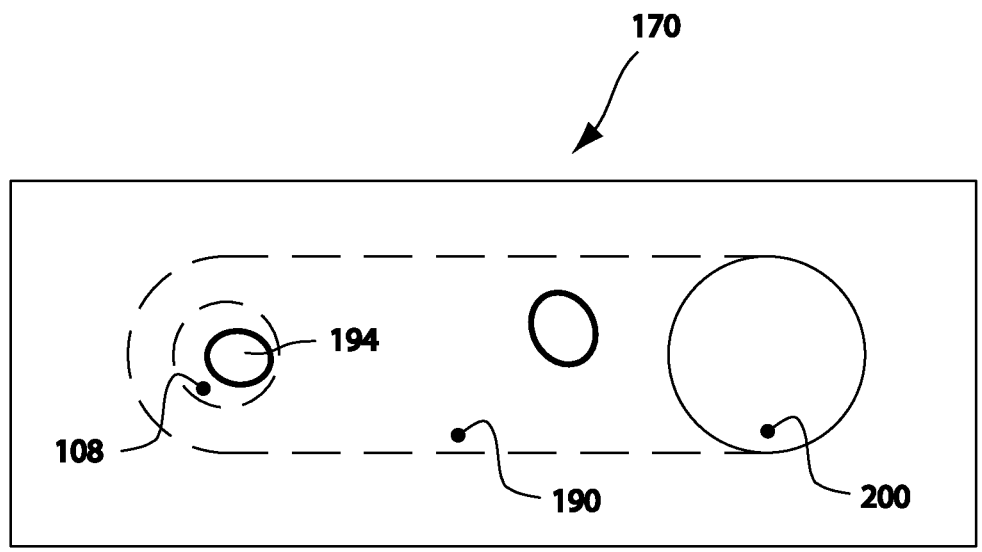
FIG. 5 is a top view of certain details of the cassette in FIG. 4.

With reference now to FIGS. 4 and 5, the multilayer cassette 170 includes a top cap layer 172, a top channel layer 174, an opaque interrogation layer 176, a bottom channel layer 178, and a bottom cap layer 180. Such layers can be stamped, e.g. die cut, or manufactured by using a laser or water jet, or other machining technique, such as micro machining, etching, and the like. In a currently preferred embodiment 170 that is used for multiplexed immunoassays, the various layers are typically made from thin polymer films, which are then bonded together to form the multilayer assembly. Exemplary cap layers 172 and 180 may be manufactured from Mylar film that is preferably substantially clear or transparent.

During assembly of a device 170, bonding may be effected by way of an adhesive applied between one or more layer, or one or more layer may be self-adhesive. It is currently preferred for channel layers 174 and 178 to be manufactured from double-sided tape. One workable tape is made by Adhesive's Research (part no. AR90445). Heat and pressure may also be used, as well as other known bonding techniques. Desirably, the thickness of at least the channel layers 174 and 178 is approximately on the order of the characteristic size of particles of interest to promote single-file travel of particles through an interrogation zone. For example, a workable thickness of such layers in currently preferred devices used to interrogate latex bead populations typically ranges between about 35 microns and about 300 microns.

Exemplary cassette 170 includes a plurality of electrodes 182, 184, 816, 188 that are disposed in channels 190, 192 to permit interrogation of particles (e.g. 194) in an interrogation zone (e.g. including tunnel 108) using the Coulter principle. For example, impedance may be measured between electrodes, such as electrode 184 and electrode 186 (as indicated at $V_A$ and $V_B$), while a time-varying electrical signal is applied by signal generator 196 between electrodes 182 and 188.

Illustrated embodiment 170 includes a window 196 to admit radiation from a source 142 to the interrogation zone. Window 198 is included to permit propagation of stimulated radiation toward detector 144. Therefore, as fluid enters port 200 and flows through the interrogation zone toward exit 202, the particles entrained in the fluid may be interrogated using the Coulter principle, and/or Stokes' shift or other radiation emission phenomena.

Figure 6:
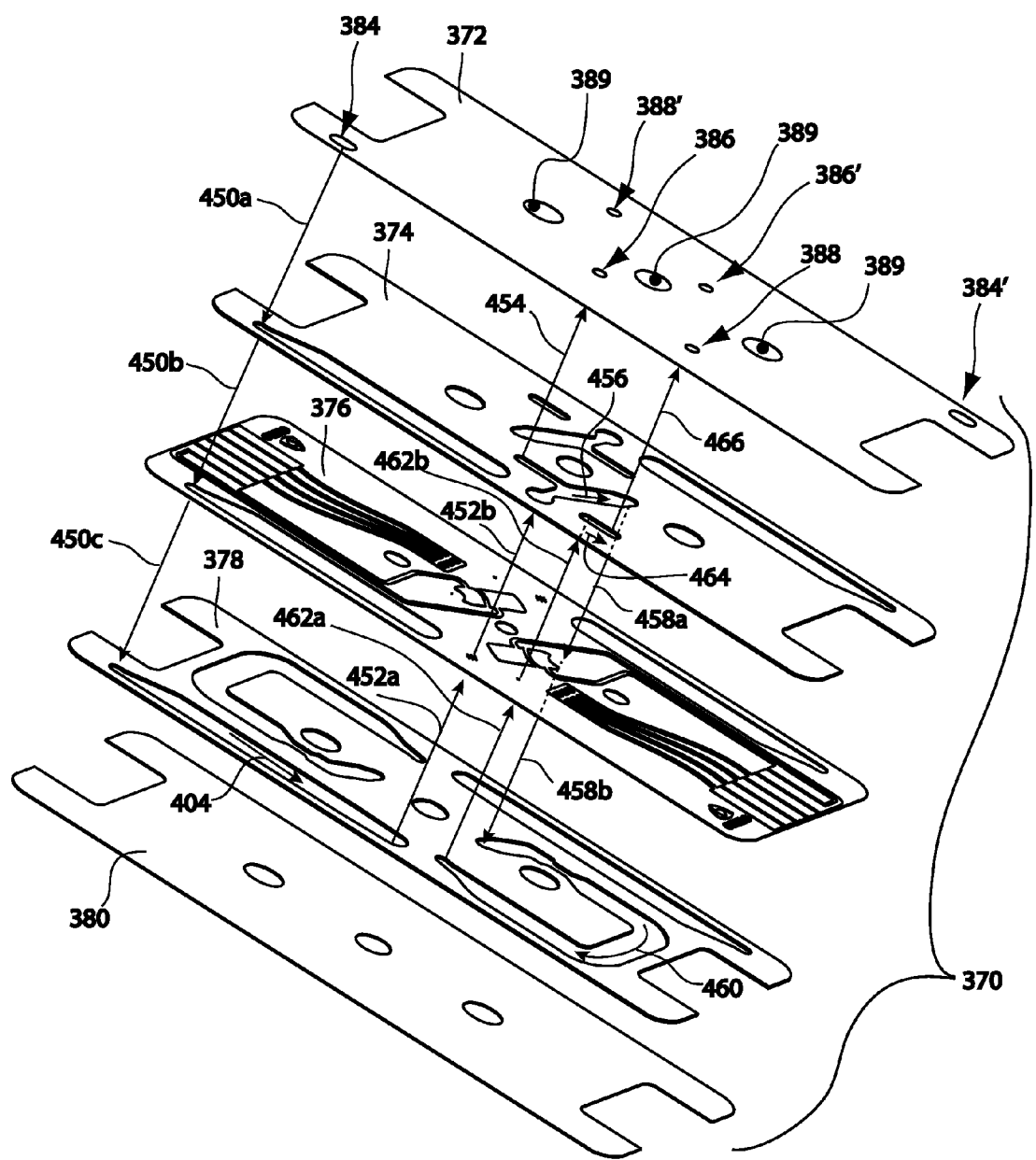
FIG. 6 is an exploded assembly view in perspective of a currently preferred cassette for use in certain embodiments of the invention.

Elements of a currently preferred sensor arrangement that may be structured as a cassette, or cartridge, are illustrated with reference to FIGS. 6-10. An exemplary such sensor arrangement is assembled from a plurality of thin film layers that are stacked and bonded together to form a multilayer cartridge, generally 370. With reference to FIG. 6, cartridge 370 includes top cap layer 372, top channel layer 374, interrogation layer 376, bottom channel layer 378, and bottom cap layer 380.

The currently preferred top cap layer 372 and bottom cap layer 380 may be made from 0.005" thick transparent polyester film. Desirably, the cap layers are structured to cooperate for operable transmission of radiation through the cassette 370. That is, the top cap layer 372 may permit transmission there-through of at least excitation radiation and bottom cap layer 380 may permit transmission there-through of at least stimulated radiation. A reverse arrangement would be employed when the emission detector is disposed "above" the cassette 370, and the radiation source is disposed "below" the cassette 370. In any case, it is desirable to provide a suitable window to permit transmission of radiation operably through a cassette to permit detecting stimulated radiation from one or more particle of interest.

Workable channel layers 374 and 378 may be made from 0.010" thick double sided acrylic based adhesive film stock. In such case, the center carrier layer may be 0.007" thick polyester film with 0.0015" thick adhesive coated on each side. A currently preferred interrogation layer 376 may be made from an assortment of materials, depending upon the intended use for the particular sensor that will be constructed. A clear 0.005" thick polyester film may be used for sensors structured to interrogate impedance measurements only. It is preferred to employ an opaque polyamide film for sensors structured to interrogate impedance and fluorescence (or just fluorescence). The opaque film inherently resists transmission of undesired radiation toward the Stokes shift detection sensor.

Although such is not required, the illustrated cartridge 370 is a two-ended arrangement structured to provide duplicated structure forming first and second sensors on the same removable and reversible cassette 370. For clarity, the duplicated structures included in the illustrated second sensor are indicated with a prime. Such an arrangement permits associating the cassette 370 at a first orientation with an interrogation device, running a first test, then removing and reversing the cassette 370 to interface with the interrogation device at a second orientation to perform a second test. The first and second tests may be the same type of test, or different tests, performed on different fluid samples. It is within contemplation that the first and second tests may not be the same, and may also be performed on at least a portion of the same fluid sample. For example, fluid may be passed through one sensor arrangement to a common storage chamber before being passed through a second, or subsequent, sensor arrangement on a single alternatively structured cassette. It is within contemplation to provide a multi-ended arrangement providing a further increased number of sensors (e.g. 3, or 4, or more) on the same cassette, or cartridge.

With continued reference to FIG. 6, top cap layer 372 provides a sample loading port 384, a vent 386, and a vacuum application port 388. A plurality of over-size alignments holes 389 are also included. Alignment holes 389 are oversized to provide clearance for other precise alignment structure during assembly of the cartridge 370. Alternative precision alignment structure may be provided for certain layers, such as 372, 374, 378 and 380. Such alternative alignment structure may then be redacted from the finished cassette during a manufacturing step. Also, in certain embodiments, vent ports 386 are not included.

Figure 7:
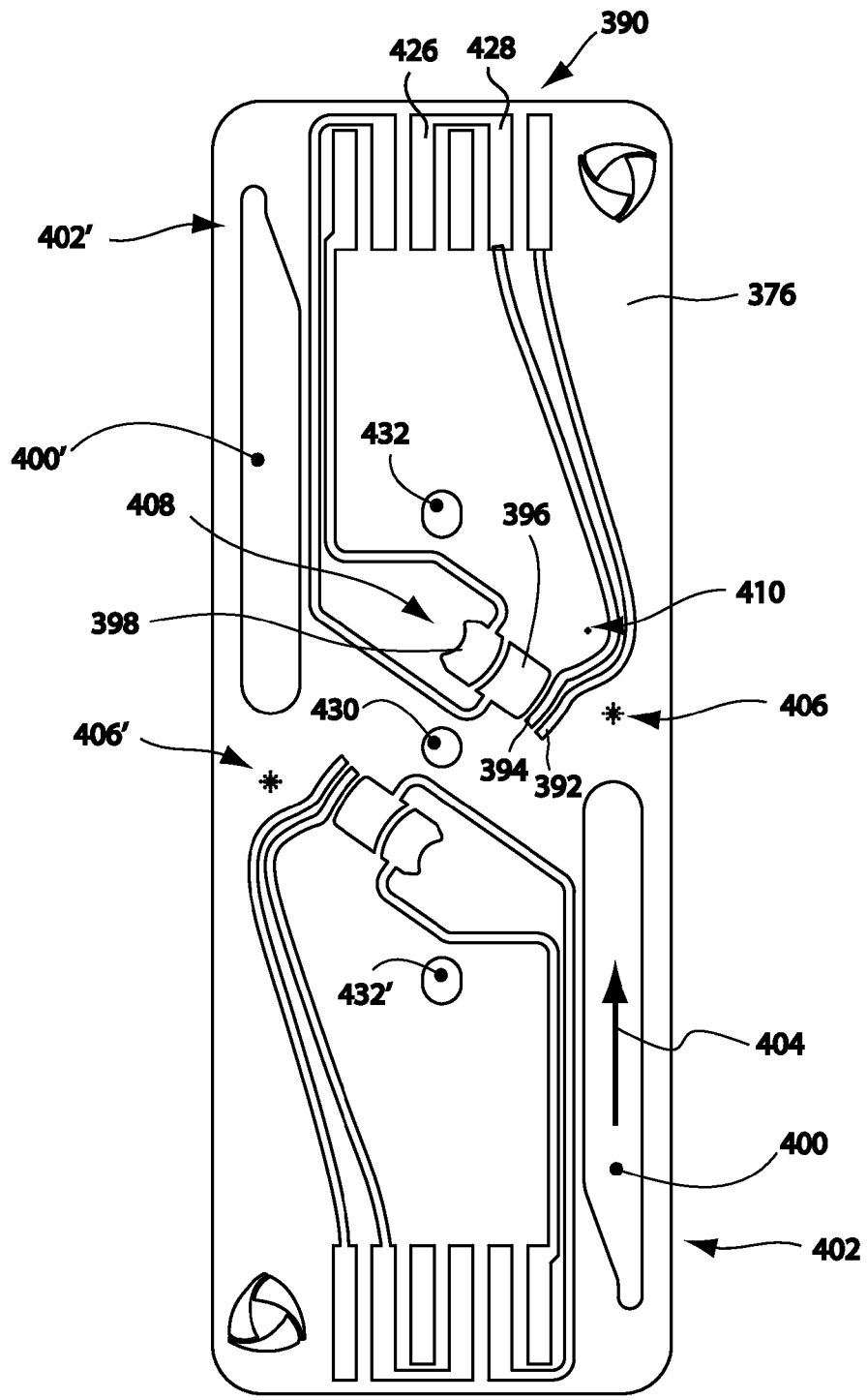
FIG. 7 is a top plan view of an interrogation layer of the cassette in FIG. 6.

With reference now to FIG. 7, interrogation layer 376 carries a plurality of surface contact electrical pads, generally indicated at 390. While alternative deposition of conductive material is operable, it is currently preferred to print the contact pads 390 and other conductive traces and structures using electrically conductive ink and a web-based screen printing process that lends itself to mass production.

As illustrated in FIG. 7, a first trigger electrode 392 and a second trigger electrode 394 are disposed upstream of first driving electrode 396 and first detection electrode 398, and may therefore detect a trailing, or fluid flow termination, boundary. Such an arrangement permits electrode 392 and 394 to operate as an electrically-based trigger that is inherently tripped by a fluid flow boundary, and can be used to terminate data collection. For example, impedance can be monitored between electrode 392 and electrode 394. In general, it is desirable for trigger electrodes to be narrow and disposed as close together as possible. An electrode area can be fairly small (e.g. 0.025"×0.065") and the current printing process can easily maintain a 0.015" spacing between printed electrodes.

With continued reference to FIG. 7, a plurality of apertures and channels are removed from the film forming interrogation layer 376. As illustrated, a partial length channel 400 is disposed to receive a fluid sample for interrogation. The sample is typically loaded at proximal end 402, and flows in the direction indicated by arrow 404, toward debris filter 406. An exemplary debris filter resists passage of undesired particulate matter toward the interrogation aperture 408. It is currently preferred to laser drill a plurality of small apertures in combination to form a sort of screen-like debris filter 406. An additional aperture structure includes fluid exit vent 410. Desirably, exit vent 410 is structured to permit application of vacuum to cause fluid flow through passages in the cartridge 370, and to apply capillary attraction to resist flow of fluid beyond the vent 410, itself.

Figure 8:
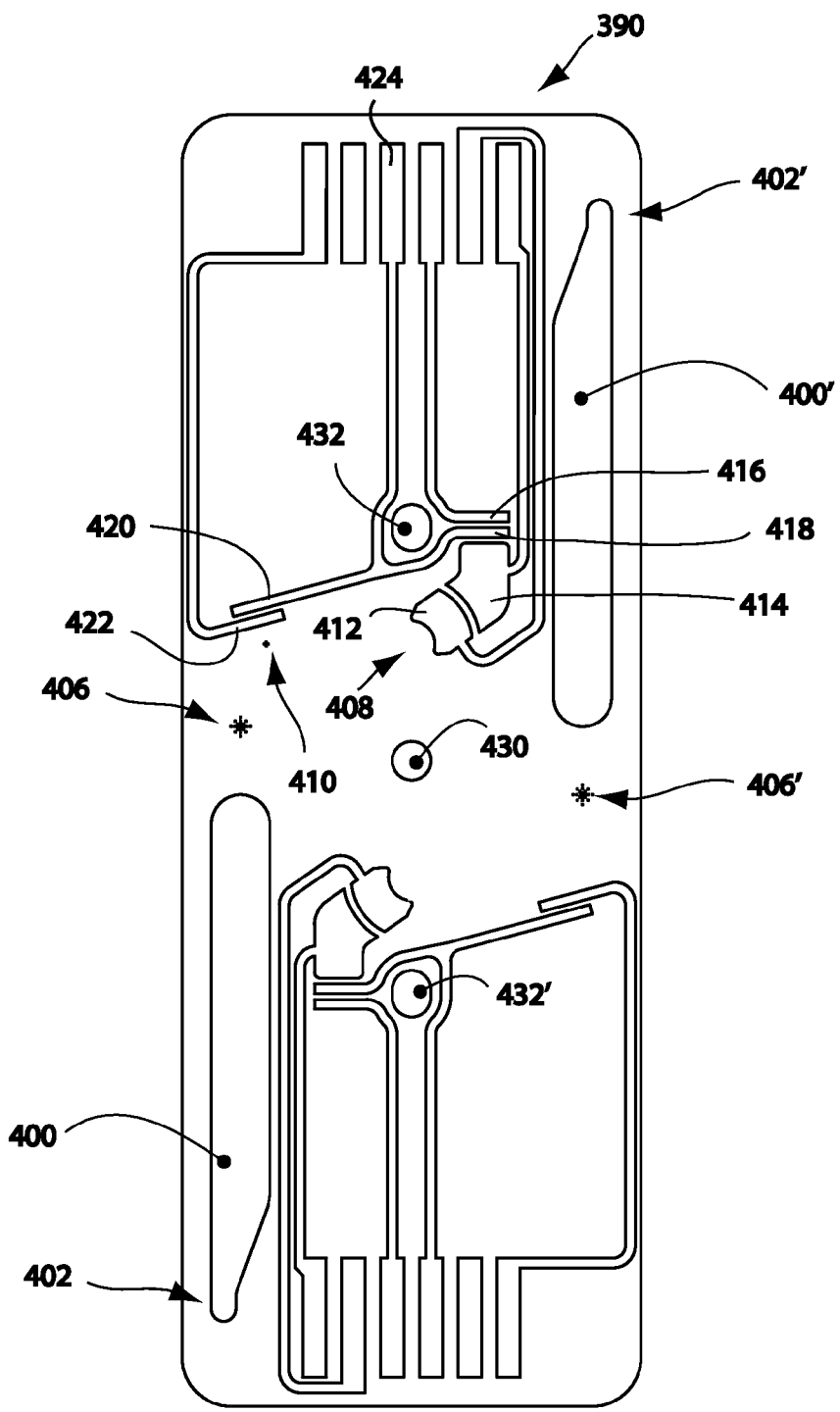
FIG. 8 is a bottom plan view of the interrogation layer in FIG. 7.

With particular reference to FIG. 8, the other side of interrogation layer 376 includes additional electrical contact pads, generally 390. In the illustrated embodiment, the electrical contact pads 390 disposed on one side are not disposed in electrical communication with electrical contact pads 390 on the other side, although such may be convenient in certain cases. Electrically conductive traces extending from the contact pads are configured to provide a second interrogation electrode 412 and a second driving electrode 414.

Still with reference to FIG. 8, a third trigger electrode 416 and a fourth trigger electrode 418 are disposed down stream of second detection electrode 412 and second driving electrode 414 and may therefore detect a fluid flow arrival boundary. Such an arrangement permits trigger electrode 416 and trigger electrode 418 to operate as an electrically-based trigger that is inherently tripped by a fluid flow boundary, and can be used to begin data collection during the test of a fluid sample.

A fifth trigger electrode 420 and a sixth trigger electrode 422 are also illustrated in FIG. 8 as being disposed down stream of second detection electrode 412 and second driving electrode 414 and may therefore cooperate to detect a fluid flow arrival boundary at a second location. This third trigger is disposed near the vent aperture 410. Such an arrangement permits electrode 420 and 422 to operate as an electrically-based trigger that can be used to detect the "end of test" for a fluid sample when using the known volume method with respect to the volume in channel 442 and disposed between trigger or boundary detection locations.

For convenience, electrode surface contact pad 424 is in electrical communication with both of electrode 418 and 420, and can therefore be used to apply a common reference signal, such as ground. On the other side of layer 376, electrical contact pads 426 and 428 are in electrical communication and may be used in a continuity check to verify proper insertion of a sensor into engagement in a preferred interrogation device. It should be noted that certain sensors may be constructed having a different number of driving, detecting, verification, and/or trigger electrodes, or even none.

Layer 376 also includes a plurality of alignment apertures. Alignment aperture 430 is common to alignment structure used for both ends of the cartridge 370, and imposes an X-Y location at a known reference spot on the cartridge 370 with respect to a currently preferred interrogation device. Alignment slot 432 imposes substantially only a rotational orientation of an installed cartridge 370 with respect to that X-Y location. Desirably, one of the apertures 430, 432 is slotted, and the other is not. Such an arrangement is effective to provide a complete rigid body constraint in a plane, and helps to avoid binding of the cassette during its installation into, or removal from, an interrogation device. The radius of illustrated round alignment aperture 430 is 0.050". The distance between the radii of alignment slot 432 is 0.025" and the radii are 0.050". Cooperating alignment pins in the preferred interrogation device have diameters of 0.1000", and the alignment pins of the preferred interrogation device are precision ground to a tolerance of ±0.0001". Planar orientation of the cartridge is typically enforced by other clamping structure associated with the preferred interrogation device.

Figure 9:
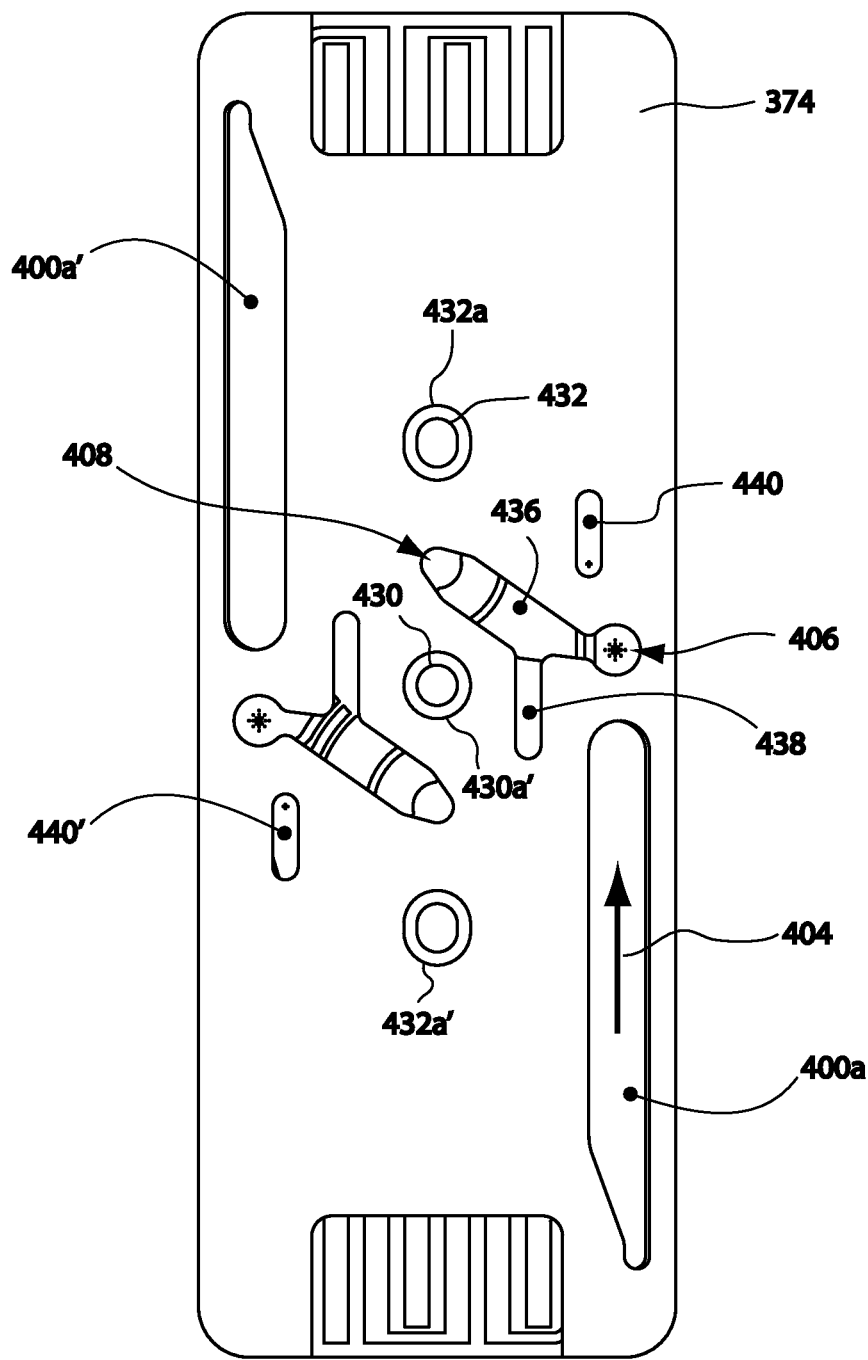
FIG. 9 is a top plan view of a partially assembled portion of the cassette in FIG. 6.

With reference now to FIG. 9, top channel layer 374 includes a plurality of channel structures. Partial-length fluid receiving channel 400a cooperates with channel 400 in layer 376 to permit introduced sample fluid to flow in the direction indicated by arrow 404. Bridge channel 436 transports fluid from debris filter 406 toward interrogation aperture 408. An optional dogleg channel portion 438 may communicate to an optional vent 386 (see FIG. 6) at the top of the cartridge 370, and facilitates loading a fluid sample into the cartridge 370. Buffer channel 440 communicates from exit vent 410 toward a vacuum port 388 (see FIG. 6) on top of the cartridge 370. Along with over-size apertures 389, alignment apertures 430a and 432a are also desirably pulled back during a manufacture step to avoid causing a potential structural interference with respect to alignment apertures 430 and 432 disposed in penetration though the interrogation layer.

Figure 10:
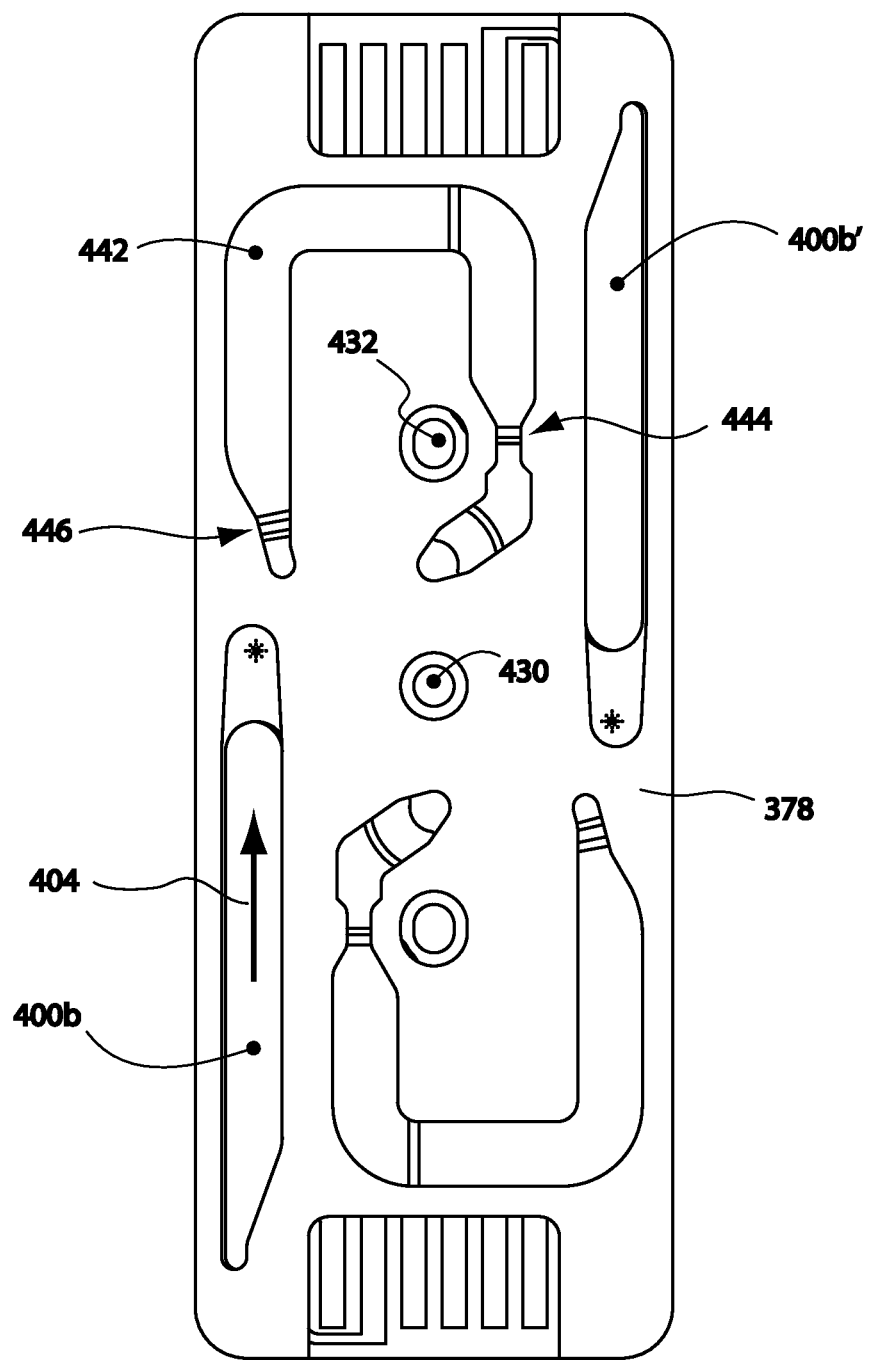
FIG. 10 is a bottom plan view of a partially assembled portion of the cassette in FIG. 6.

With reference now to FIG. 10, bottom channel layer 378 carries full-length sample receiving channel 400b. Channel 400b communicates introduced fluid underneath layer 376 to the bottom of debris filter 406. Channel 442 receive fluid downstream of interrogation aperture 408. In certain embodiments, a first electrically-based trigger, generally indicated at 444, is disposed near one end of the chamber formed by channel 442. A workable trigger may be formed between two dedicated electrodes, or sometimes between one dedicated electrode and a shared electrode. Illustrated trigger 444 in FIG. 10 is formed between electrodes 414 and 418 (see FIG. 8). A trigger at a location such as trigger 444 is operable as a "start" trigger, to begin collection of data during an interrogation of a fluid sample. It has been determined that a single impedance-detecting electrode, such as 418, cooperating with a source or driving electrode 414 is more reliable than a cooperating dedicated pair of electrodes 418, 416 disposed in very close association with a driving electrode such as 414.

A second electrically-based trigger, generally 446, may be disposed spaced apart from trigger 444 by a known volume provided by channel 442. Illustrated trigger 446 is formed by electrodes 420 and 422 (see FIG. 8). In certain cases, a second known volume may be defined by channel and aperture structure disposed between trigger 444 and an upstream trigger, such as may be formed between electrodes 292 and 294 (see FIG. 7).

Known volumetric trigger spacing and collection of data signals including a common time component or base, permit: starting and stopping test data collection; control for application of vacuum; confirmation of processing a desired sample volume; and calculation of volumetric rate of processing, among other capabilities.

With reference again to FIG. 6, the fluid flow path through cassette 370 will now be described. In one type of test, a sample is typically introduced to sample loading port 384 using a pipette instrument to accurately dispense a desired test volume, or sometimes a surplus volume. Entering fluid flow is represented by arrows 450a, 450b and 450c. Sample fluid then flows along a channel formed by channel portions 400, 400a, and 400b in the direction indicated by arrow 404. As indicated by arrows 452a and 452b, fluid flow through debris filter 406 to channel 436. Air may be passed out aperture 386, as indicated by arrow 454. During a test, fluid flows along channel 436 in the direction indicated by arrow 456. Fluid then flows through interrogation aperture 408 as indicated by partially hidden arrows 458a and 458b. Fluid flow in channel 442 is indicated by arrow 460. Fluid then flows through vent 410 as indicated by arrows 462a and 462b. Fluid then flows along channel 440 in layer 374, in the direction indicated by arrow 464, before potentially exiting vacuum port 388, indicated by arrow 466. In certain cases, channel 440 may provide a buffer to resist escape of fluid from a cartridge 370.

Typically, an Excimer laser is used to form the interrogation apertures 408 and alignment apertures 430 and 432. A DPSS laser is generally used to form all of the other channel and aperture structure (filters, vents, channels, etc.). The excimer can cut the currently preferred 44 μm diameter interrogation aperture 408 within ±2 microns. Repeatability of the DPSS is more like plus/minus 5 microns. The large alignment holes 430, 432 are manufactured (laser cut) with extreme precision relative to the laser drilled interrogation aperture 108. Use of the more accurate laser allows the interrogation aperture 408 to be mechanically aligned, from cassette to cassette, to the laser beam of a cooperating docking station of a preferred interrogation device with an accuracy of about 20 µm to 50 µm. Here, "accuracy" means that the center of the aperture is disposed within a repeatable "accuracy" radius of the theoretical centerline of an interrogation zone provided by a cooperatingly structured interrogation device.

Figure 11:
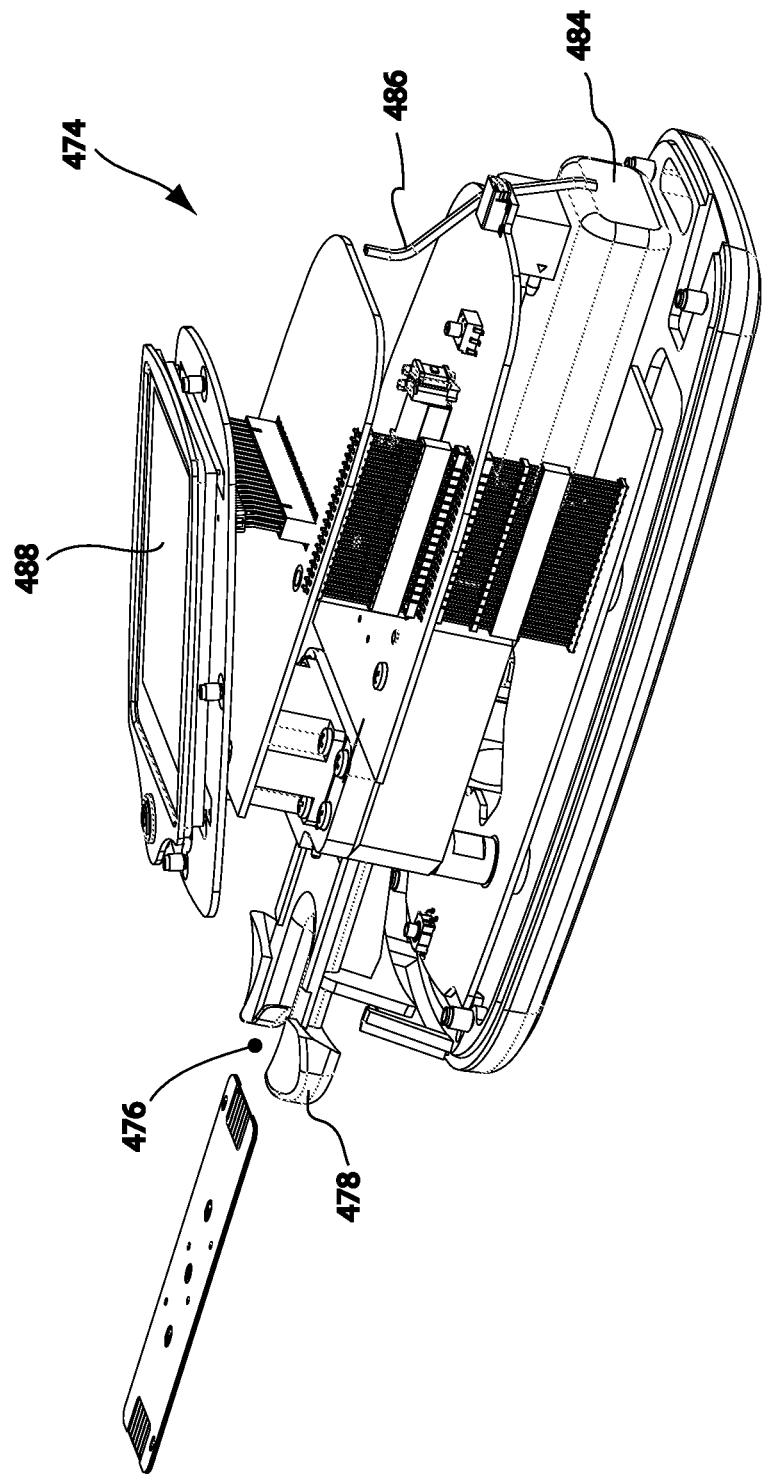
FIG. 11 is a perspective view of a workable interrogation platform.
Figure 12:
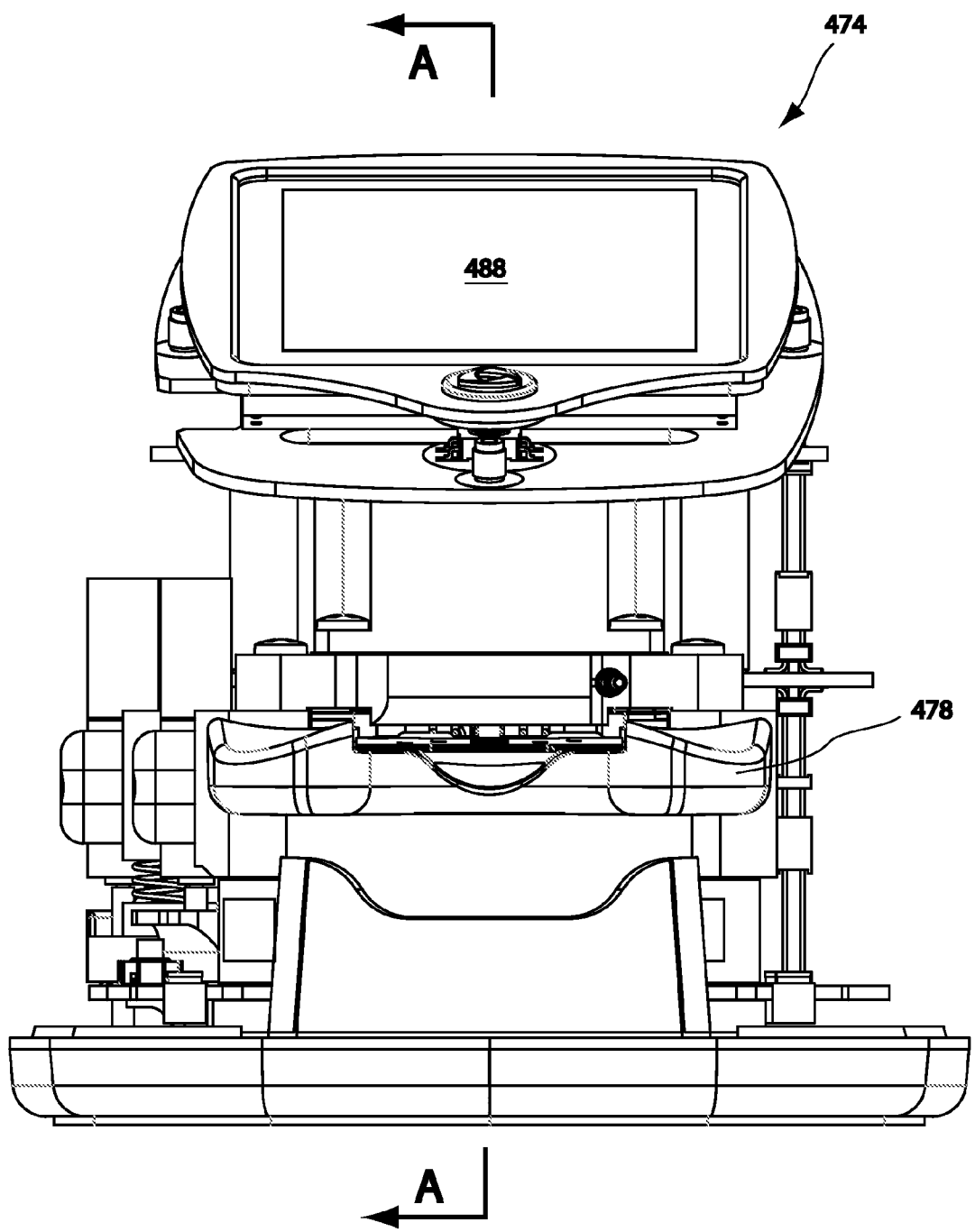
FIG. 12 is a front view of the interrogation platform in FIG. 11.
Figure 13:
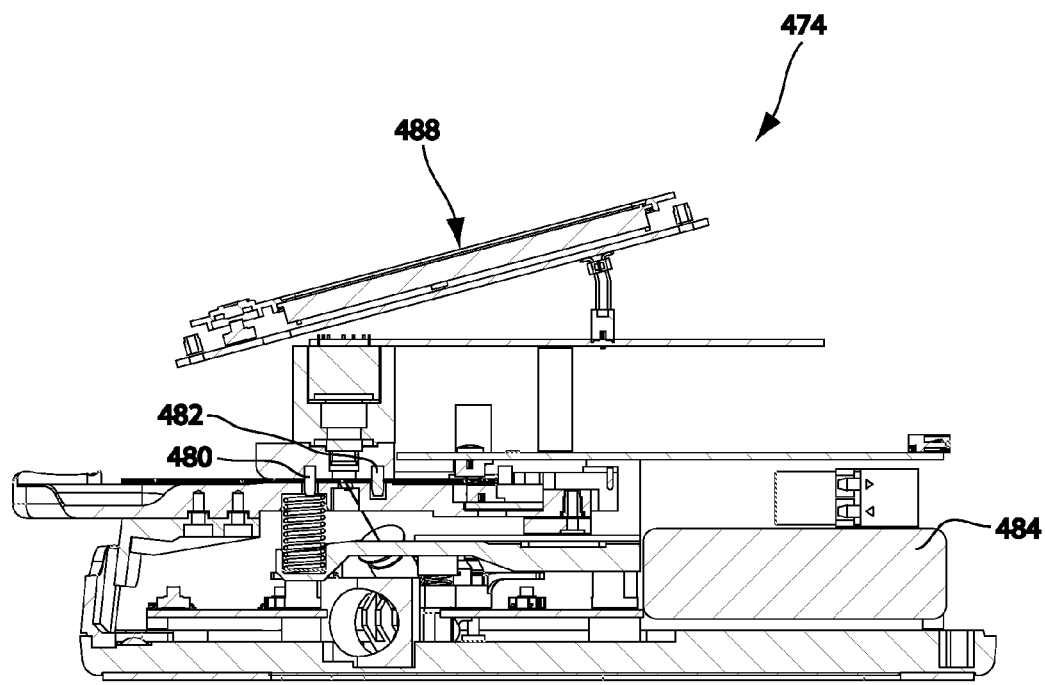
FIG. 13 is a cross-section view in elevation, taken at section 13-13 in FIG. 12, and looking in the direction of the arrows.

With reference now to FIGS. 11 through 13, an interrogation platform, generally 474, is desirably structured to cooperate with a cassette to permit particle interrogation. Illustrated interrogation platform 474 is representative of a table-top device, and includes a docking area 476 in which to receive a cassette, such as cassette 370. Guide structure 478 helps to orient the cassette in a plane, and pins 480, 482 orient the cassette in that plane. Illustrated vacuum pump 484 represents an exemplary device operable to urge fluid motion through an installed cassette 370. Note that only a portion of a vacuum line 486 is illustrated in FIG. 11. Such vacuum line 486 would, of course, be placed into operable communication with an installed cassette.

A table-top platform, such as platform 474, typically includes electronic circuitry effective to interface with a cassette and operable to interrogate particles in a fluid sample as that sample is flowing through a portion of the cassette. A workable interface includes an electrical edge connector structured to cooperate with surface contact electrodes of a cassette, such as electrodes 390 (see FIG. 7). Desirably, the electronic circuitry is operable to detect a Coulter effect, and generate a signal in correspondence with the Coulter effect. Further, certain platforms include circuitry operable simultaneously to detect radiation emanating from an interrogation zone included on the cassette. Preferred interrogation platforms also include calculation structure, such as a microprocessor and associated memory, operable to convert generated input signals into qualification and/or quantification results for one or more fluid sample. As illustrated, a display device 488 may be disposed to show the results of an interrogation.

In general, a method according to the instant invention encompasses performing multiplexed bead-based immunoassays using a microfluidic cassette capable of detecting a particle passing in substantially single file through an interrogation zone. A preferred cassette (e.g. one of cassette 100, 170, 370) is capable of generating a Coulter effect signal responsive to a characteristic of the particle. A fluid sample may be prepared by associating appropriately-receptive beads of different sizes to particles of interest. In the case of processing a biological sample of interest, a plurality of beads of different sizes (such as may be selected from 2, 3, 4, 5, 6, 7, 8, 9, 10, 11, 12, 15, etc.) may individually (i.e., by size group or sub-population) be labeled with an antigen specific to an antibody or protein of interest.

A first multiplexing option may be based on bead size, in which case the intensity of the Coulter effect signal is used to sort or characterize the particles. The plurality of different detectable bead sizes, alone, permits multiplexed analysis of a processed fluid sample. A second multiplexing option may be based on detection of Stokes' shift phenomena, or even simply emission intensity, in which case particles may be characterized responsive to intensity of the resulting radiation-generated signal. The first and second multiplexing options may be employed together to populate an array of particle characteristics.

In an exemplary process, beads of defined spectral properties are conjugated to protein-specific capture antibodies and added to samples. Samples generally include standards of known protein concentration, control samples, and test samples. Target protein binds to the capture antibodies over the course of a 2-hr incubation. After washing the beads, protein-specific, biotinylated detector antibodies are added and incubated with the beads for 1 hr. Next, excess biotinylated detector antibodies are removed, and streptavidin-conjugated fluorescent protein, R-Phycoerythrin (SAV-RPE), is added and incubated for 30 min. SAV-RPE binds to the biotinylated detector antibodies, forming a four-member, solid-phase sandwich. After washing to remove unbound SAV-RPE, the beads in each sample are analyzed with an interrogation platform. By monitoring the spectral properties of the beads and the amount of associated R-Phycoerythrin (RPE) fluorescence, the concentration of one or more proteins can be determined. Calibration for test sample results may be performed using results from processing standards and/or control samples.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method, comprising:
providing a first fluid sample containing a plurality of particles that individually may carry one or more biological label, each such label being indicative of one or more characteristic of a particle;
providing a cassette that defines a channel for fluid flow, said channel including a constriction associated with an interrogation zone sized to contain substantially not more than a single particle carried in said fluid sample, a first electrode disposed to contact fluid in said channel upstream of said constriction and a second electrode disposed to contact fluid in said channel downstream of said constriction to permit detecting a change in impedance as a particle passes through said interrogation zone effective to indicate the presence of substantially not more than said single particle in said interrogation zone, whereby fluid flow through said constriction is orthogonal to a direction in which fluid flows past said first electrode said second electrode;
loading said first fluid sample into said cassette;
installing said cassette in operable registration with an interrogation device comprising:
a detector configured to detect a change in impedance generated due to presence of a detected particle in said interrogation zone;
a vacuum source effective to urge fluid flow through said channel; and
radiation evaluation elements, including a source of excitation radiation, a radiation detector, and a filter effective to resist impingement of excitation radiation onto said detector, said radiation evaluation elements being arranged to cooperate with an installed said cassette to permit radiation-based interrogation of said detected particle that is present in said interrogation zone;
using said vacuum source to urge flow of said first fluid sample through said cassette while performing an interrogation using said interrogation device to interrogate a portion of said first fluid sample as said first fluid sample is flowing through said cassette; and performing a multiplexed quantification on particles in said portion of said first fluid sample using results of said interrogation, wherein said cassette comprises:

a plurality of stacked thin film substantially planar layers forming the cassette providing structure defining a fluid path disposed inside said cassette, said path comprising:

a first portion disposed parallel to, and within, said layers;

a second portion provided by a tunnel passing through an interrogation layer, said tunnel being sized to urge particles entrained in a carrier fluid into substantially singlefile travel through a particle interrogation zone; and a third portion disposed parallel to, and within, said layers, said first portion and said third portion being disposed on opposite sides of said particle interrogation zone, and wherein said interrogation comprises:

generating a signal based on a change in impedance corresponding to a presence of a first particle in said interrogation zone;

monitoring for presence of a Stokes' shift radiation from substantially not more than said first particle;

generating a Stokes' shift signal corresponding to said Stokes' shift radiation; and using a characteristic of said Stokes' shift signal to characterize said first particle.

2. The method of claim 1, wherein said interrogation comprises:

generating a plurality of signals based on changes in impedance corresponding to a population of particles passing through said interrogation zone; and characterizing individuals of said population of particles based on measured intensities of said signals.

3. The method of claim 1, wherein said interrogation comprises:

generating a signal based on a change in impedance corresponding to a presence of a first particle in said interrogation zone;

monitoring for presence of radiation at one or more characteristic frequency that emanates from said interrogation zone due to presence of said first particle;

generating a radiation signal corresponding to said radiation; and using a relative intensity of said radiation to quantify the amount of bound protein or antigen present on said first particle.

4. The method of claim 3, wherein said monitoring for presence of radiation comprises:

detecting fluorescence propagating from said interrogation zone effective to characterize an analyte in said fluid; and simultaneously detecting a second fluorescence signal propagating from said interrogation zone effective to quantify an amount of bound protein or antigen on said first particle.

5. The method of claim 1, wherein:
said particle comprises a protein.

6. The method of claim 1, wherein:
a biological label carried by a particle in said first fluid sample comprises an antibody-coated bead.

7. The method of claim 1, wherein:
a biological label carried by a particle in said first fluid sample is selected from a plurality of appropriately-receptive beads having different sizes, each size corresponding to a different characteristic that may be present in one or more particle in said fluid.

8. The method of claim 1, wherein:
a biological label carried by a particle in said first fluid sample is selected from a plurality of appropriately-receptive beads having different fluorescent intensities, each intensity corresponding to a different characteristic that may be present in one or more particle in said fluid.

9. The method of claim 1, wherein:
a biological label carried by a particle in said first fluid sample is selected from a plurality of appropriately-receptive beads having different fluorescent characteristic wavelengths, each characteristic wavelength corresponding to a different characteristic that may be present in one or more particle in said fluid.

10. The method of claim 1, wherein:
a biological label carried by a particle in said first fluid sample comprises an aptamer-coated bead.

11. The method of claim 1, wherein:
a biological label carried by a particle in said first fluid sample comprises a protein-coated bead.

* * * * *